United States Patent [19]

Phillips

[11] 4,374,146
[45] Feb. 15, 1983

[54] TOPICAL INFLAMMATORY PHARMACEUTICAL FORMULATIONS

[75] Inventor: Arthur P. Phillips, Raleigh, N.C.

[73] Assignee: Burroughs Wellcome Co., Research Triangle Park, N.C.

[21] Appl. No.: 323,803

[22] Filed: Nov. 23, 1981

[30] Foreign Application Priority Data

Nov. 26, 1980 [GB] United Kingdom ............... 8037873

[51] Int. Cl.$^3$ ............................................ A61K 31/36
[52] U.S. Cl. .................................................. 424/282
[58] Field of Search ....................................... 424/282

[56] References Cited

PUBLICATIONS

Chem. Abst. 82-11947h (1975).

Primary Examiner—Stanley J. Friedman
Attorney, Agent, or Firm—Donald Brown

[57] ABSTRACT

A compound of the formula (I) may be prepared by known methods and may be used in the treatment of pain, inflammation or pyresis in mammals, by administration of the compound alone or in a pharmaceutical formulation suitable for administration to a mammal in need thereof.

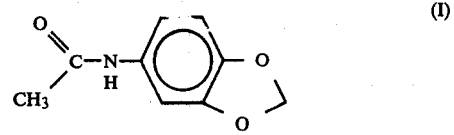

(I)

8 Claims, No Drawings

TOPICAL INFLAMMATORY PHARMACEUTICAL FORMULATIONS

This invention is directed to a method of treating of pain, inflammation of pyresis in mammals by the administration of a compound of formula (I) either alone or in a pharmaceutical formulation suitable for administration to a mammal in need thereof, and to methods of preparing such formulations.

The compound of formula (I):

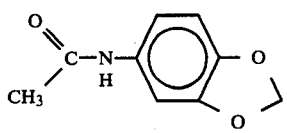

namely, N-(1,3-benzodioxol-5-yl)acetamide which may also be named 3,4-methylenedioxy acetanilide, was disclosed by Rupe et al (1900) in Ber. 33, 3404 and in Beilstein, 19, 328 as a chemical intermediate.

It has now been found that the compound of formula (I) has analgesic, anti-inflammatory and antipyretic activity. The compound is a derivative of the known analgesic phenacetin, namely p-ethoxyacetanilide. Phenacetin is known to exhibit unfavourable effects as shown in Table IV B. Therefore, it could have been expected that the compound of formula (I) would also exhibit similar unfavourable effects.

However, the compound of formula (I) has, surprisingly, not been shown to produce histopathological evidence of hepatic or renal damage in the rat or mouse; or to deplete hepatic glutathione in the mouse; or to produce methemoglobinaemia after high oral doses in rats, although the compound has produced methemoglobinaemia in dogs at high dose levels but phenacetin produces severe methemoglobinaemia at relatively low dose levels. In addition, since the compound of formula (I) is not a prostaglandin synthetase, lipoxygenase or peroxidase inhibitor, it does not produce the gastric damage or platelet aggregation inhibition associated with aspirin-like drugs.

The compound of formula (I) (hereinafter referred to as the 'active compound') has been found to have analgesic activity as shown by the acetic acid writhing assays (Koster et al, in Proc. Soc. Exp. Biol. Med, (1959), 18, 412; Vinegar et al in Handbook of Experimental Pharmacology, (1978), 50 (2); Ch. 26, Anti-Inflammatory Drugs, Ed. J. R. Vane and S. H. Ferreria) and the trypsin hyperalgesic assay (Vinegar et al in Eur. J. Pharmacol, (1976), 37, 23). In this respect, the active compound exhibits different pharmacological properties from aspirin which is essentially inactive in the latter assay (see Table I). In addition, the analgesic activity of the active compound is believed to be unlike that of morphine and codeine since: the active compound is inactive in the hot plate assay for strong analgesic activity, a test in which both codeine and morphine are active; its activity is not inhibited by naloxone; it does not bind to opiate receptors in vitro; and it is inactive in the trypsin hyperalgesic assay when injected intracerebroventricularly (I.C.V.—i.e. directly into the brain).

The active compound has been found to have anti-inflammatory activity in the rat comparable with aspirin as shown in the carrageenin pleurisy assay (Vinegar et al in Eur. J. Rheumatol. and Inflam., (1978), 1, 204), (see Table II).

The active compound was found to have antipyretic activity in the rat comparable with aspirin and phenacetin, according to the yeast-induced hyperthermia assay, (see Table III).

The active compound may be prepared by any method known in the art, for example by the method of Rupe et al in Berichte (1900) 33, 3404. For example, the active compound may be prepared by acetylation of N-(1,3-benzodioxol-5-yl)amine (which may also be named 3,4-methylenedioxy aniline, hereinafter referred to as compound (II)) with a suitable acetylating agent such as acetic anhydride in a suitable solvent such as diethyl ether.

Compound (II) may itself be prepared according to the method described by Rupe (op cit), that is, from the corresponding acid amide ((3,4-methylenedioxy)benzene carbamide, compound (III)) by a Hoffmann elimination reaction. Alternatively, compound (II) may be prepared by reduction of the corresponding nitro-compound ((3,4-methylenedioxy)nitrobenzene, compound (IV)). For example: by catalytic reduction in the presence of hydrogen and a suitable catalyst such as palladium or platinum; by the use of a mineral acid such as hydrochloric acid in the presence of a metal such as zinc or tin; or by a hydrazine such as hydrazine hydrate in the presence of a suitable catalyst such as palladium or platinum. The acetylation of compound (II) may conveniently be effected either during or after the reduction of compound (IV).

Compound (IV) may itself be prepared by nitrating methylenedioxybenzene (hereinafter referred to as compound (V)) by standard methods, for example, by mild nitration with a mild nitrating agent such as nitric acid together with a weak acid such as acetic acid.

The active compound may be used in the relief, treatment or prophylaxis of pain, inflammation or fever, in a mammal, including man, such as: that resulting from headache, toothache, pain following general dental procedures, oral and general surgery, dysmenorrhea, myalgia, pain of unresectable cancer, joint and peripheral nerve disorders, rheumatoid arthritis, rheumatoid spondylitis, osteoarthritis, gouty arthritis and other arthritic conditions, pyresis and other conditions associated with pain, inflammation and fever.

The amount of active compound required for use in the above conditions will, of course, vary with the route of administration, the condition under treatment and the mammal undergoing treatment, and is ultimately at the discretion of the physician. However, a suitable analgesic, anti-inflammatory and/or antipyretic oral dose of the active compound for a mammal is in the range of from 1 to 100 mg per kilogram bodyweight per day; a typical dose for a human recipient being 30 mg/kg body weight per day.

The desired dose is preferably presented as between one and three sub-doses administered at appropriate intervals throughout the day. Thus, when two sub-doses are employed each will lie in the range of from 0.5 to 30 mg/kg body weight; a typical dose for a human recipient being 10 mg/kg body weight.

While it is possible for the active compound to be administered (at an appropriate dose) alone as the raw chemical, it is preferable to administer it as a pharmaceutical formulation. Formulations of the the present invention, both for veterinary and for human medical use, comprise the active compound in association with a pharmaceutically acceptable carrier therefor and optionally any other therapeutic ingredient. The carrier(s) must be 'pharmaceutically acceptable' in the sense of being compatible with the other ingredients of the formulation and not deleterious to the recipient thereof.

The formulations of the present invention include those suitable for oral, rectal or parenteral (including subcutaneous, intraperitoneal, intramuscular and intravenous) administration.

The formulations may provide for rapid, prolonged or delayed release of the active compound to effect different rates of onset and/or duration of therapeutic effect.

The formulations may be prepared by any of the methods well known in the art of pharmacy. All methods include the step of bringing the active compound into association with a pharmaceutically acceptable carrier. In general, the formulations are prepared by uniformly and intimately bringing the active compound into association with a liquid, a semi-solid, a bulk solid or a polymeric material, or a combination thereof, and then forming the product into desired formulation.

Formulations of the present invention suitable for oral administration may be presented in the form of discrete units such as capsules (soft or hard gelatin), cachets, tablets (coated or uncoated), lozenges or boluses, each containing a predetermined amount of the active compound; or as solution or a suspension of the active compound in an aqueous or a non-aqueous liquid, or a combination thereof, such as: a syrup, an elixir, a draught, a solution, a suspension, a linctus or a drench; an oil-in-water emulsion, a water-in-oil emulsion or a multiple emulsion; a paste or a gel.

A tablet, lozenge or bolus may be made by compression, fusion or moulding of the active compound optionally with one or more carrier(s). The active compound may be mixed with a diluent selected from sugars, starches, celluloses, inorganic powders and granular solids, and optionally mixed with a further carrier selected from: binders such as starches, polymeric pyrrolidone derivatives, gums of natural or synthetic origin; disintegrating agents such as starches or starch derivatives, ion exchange resins, cellulose or cellulose derivatives; lubricants such as inorganic stearates, fatty acids, polymers, natural or synthetic waxes or talcs; wetting agents such as anionic, cationic or non-ionic surface active agents; stabilising agents such as antioxidants or antimicrobial preservatives; buffering agents such as suitable organic or inorganic salts; and colours such as lakes or soluble dyes of synthetic or natural origin. The ingredients may be directly compressed together in a suitable machine or subjected to a precompression process (for example, roller compaction or compression followed by subdivision) to provide a relatively free-flowing powder or granules, and thereafter the powder or granules compressed following additional admixture with a suitable carrier selected from disintegrating agents, binders and lubricants. Alternatively, the ingredients may be aggregated into granules prior to compression, by mixing with a suitable fluid such as water, an alcohol or a solution of binding agents in either of the foregoing, followed by drying and subdivision. Aggregation may also be achieved by rolling, tumbling or vibrating the ingredients in suitable machinery. The ingredients may also be moulded in a suitable machine following their admixture, and mixed with a suitable binding agent in solution or suspension in an aqueous or non-aqueous fluid. Or the ingredients may be subjected to a sintering or polymerising process in a suitable machine.

The resulting tablets, lozenges or boluses may be coated with sugar or film coats. Sugar coats comprise sucrose or another sugar, optionally in combination with one or more carrier(s) selected from: inorganic materials such as talcs, calcium carbonate, titanium dioxide; gums such as acacia, tragacanth, cellulose derivatives, gelatin; isolating agents such as shellac, sandarac or methacrylate derivatives; colours (as described above) and polishing agents such as beeswax or carnauba wax. Film coats may comprise cellulose derivatives; polymeric materials such as methacrylates; and fatty acids and fatty acid esters; optionally comprising a wetting agent (as described above) or a platicizer selected from glycerol and polyethylene glycols. Sugar or film coats may be applied to the tablets in suitable machinery using processes such as par coating, fluidised bed coating or another coating process.

The coating agent may be constituted so as to provide rapid release of the active compound from the tablet, the lozenge or the bolus; or, alternatively, so as to modify the rate of release of the active compound following oral administration, to present the active compound to a part or parts of the digestive tract in a continuous, intermittant or delayed manner. Additionally, the active compound with carrier(s) may be processed suitably prior to compression or moulding to permit a modified rate of release of the active compound from the uncoated or coated tablet, lozenge or bolus in either an intact or disaggregated form.

A hard gelatin capsule may be made by filling the active compound, optionally mixed with one or more carrier(s) such as those listed above, using suitable machinery, into shells made of gelatin together with any suitable additional materials selected from: preservatives; humectants such as sorbitol, sucrose or glycerol; and colouring agents (as described above). The active compound, optionally mixed with one or more carrier(s), may be formed into granules by using a wet-mixing precompression, compression and subsequent subdivision or granulation process; or formed into pitules, pellets or aggregates, either uncoated or coated, prior to being filled into the gelatin shells.

A soft gelatin capsule may be prepared by filling, using suitable machinery, a solution or suspension of the active compound in an aqueous or a non-aqueous fluid selected from: alcohols, glycols, fatty acids, oils of natural origin such as olive oil, arachis oil, sunflower oil or corn oil and mixtures thereof, into flexible shells comprising gelatin together with any suitable additive selected from sorbitol, glycerin, and antioxidants, colours and antimicrobial substances (as described above).

A solution, a syrup, a suspension, a linctus, an elixir, a draught or a drench may be made by adding the active compound to an aqueous or organic solution or other fluid which may contain a sugar such as sucrose or sorbitol and which may be added to or compounded with any other carrier selected from preservatives such as sorbic acid and parabens; flavouring agents of natural or synthetic origin; suspending agents such as cellulose derivatives; natural gums such as xanthan gum, acacia, tragacanth, silicacious materials; colouring agents such as soluble or dispersed pigments or dyes of natural or synthetic origin, and wetting, buffering or solubilising agents such as those described above. Some of these carrier(s) may increase the stability or solubility of the active compound or of any other carrier.

An emulsion may be made by adding the active compound in solution or suspension in an aqueous or non-aqueous fluid with the aid of suitable machinery, to an oil of natural origin such as corn oil, or arachis oil, or to a processed oil such as liquid paraffin. The emulsion so formed may be an oil-in-water or water-in-oil emulsion or a multiple emulsion of varying rheological property and may incorporate any suitable emulgent or emulsifying agent into either or both the aqueous or non-aqueous phase prior to emulsification. Suitable emulsifying agents include natural gums such as non-ionic surface active agents such as sorbitan esters or polyoxyethylene derivatives thereof. Suspending agents such as natural gums, cellulose derivatives or inorganic materials such as silicaceous silicas may be included in the emulsified products. The emulsion may be so prepared to provide a pourable cream or a semi-solid paste.

A gel may be made by dispersing the active compound in an aqueous or non-aqueous fluid to which has been added a suitable gelling agent such as a natural gum a cellulose derivative such as carboxymethyl cellulose or its sodium salt, microcrystalline cellulose; an inorganic substance in finely divided form such as fumed silicon dioxide; or a fatty acid salt of an inorganic material such as aluminium stearate.

Alternatively, formulations for oral administration may be presented in the form of the bulk active compound optionally with one or more carrier(s) which are subsequently measured out, prior to dosing, in convenient amounts. Such formulations may be simple admixtures of the active compound with the carrier(s) presented in sachets or suitable bulk containers or subjected to a suitable process to provide the mixture in the form of granules or a granulated powder. These formulations may be diluted with a suitable fluid such as water or sugar syrup, or mixed with food or beverage, prior to administration.

Formulations for rectal administration may be presented in the form of compressed tablets, water-miscible, water-soluble or water-insoluble suppositories or in the form of soft gelatin capsules. Compressed tablets for rectal administration may be made by a process similar to that used for the preparation of a tablet, a lozenge or a bolus for oral administration and so shaped to permit convenient entry into and retention by the rectum. Suppositories may be made by preparing a solution or suspension of the active compound in a wax or fat such as cocoa butter, triglycerides, coconut oil, palm kernal oil or fatty acids, to which may be added suitable antioxidants such as propyl gallate, butylated hydroxyanisole, butylated hydroxytoluene, and forming them into a suitable shape. Alternatively, the active compound may be distributed in a mixture of polyethylene glycols or any other suitable water-miscible semi-solid or solid substance which is capable of miscibility with the aqueous contents of the rectum. The mixtures may be extruded, moulded or compressed into a suitable shape, using suitable machinery. Alternatively, the active compound may be prepared, compounded and incorporated into a soft gelatin capsule using a process similar to that used to prepare soft gelatin capsules for oral administration.

Formulations for parenteral use may be conveniently presented in single-dose or multi-dose containers prepared so as to exclude or eliminate the presence of micro-organisms.

An injection for intravenous, subcutaneous or intraperitoneal administration may be made by dissolving or suspending the active compound in an aqueous or non-aqueous fluid or a combination thereof. Suitable non-aqueous fluids may include alcohols. The solution or suspension of the active compound may also contain additional ingredients selected from: antimicrobial substances such as chlorocresol, phenol, chlorobutol; buffering agents such as organic or inorganic salts or acids; and any other substance required to increase the solubility of the active compound and other ingredients. The solution or suspension of the active compound may be sterilised by filtration or by subjection to a heat process and distributed into single-dose plastic or glass ampoules or into multidose containers.

An intramuscular injection may be prepared by incorporating the active compound in a solution as a suspension in an aqueous or non-aqueous fluid. Suitable non-aqueous substances include glycofural, arachis oil, maize oil and benzyl alcohol, to which may be added ingredients selected from suspending agents such as pyrrolidinone derivatives; antimicrobial substances such as phenols or parabens; wetting agents such as anionic, cationic or non-ionic surface active agents, and buffering agents such as organic or inorganic salts and acids. The solution or suspension is sterilised by filtration or subjection to a heat process and distributed into single or multidose containers. The carrier(s) present in formulations for intramuscular administration may or may not alter the solubility of the active compound or other ingredients therein and/or alter their rate of diffusion from the site of injection such that rapid or modified release of the active compound may occur following administration.

Therefore, according to the present invention there are provided:

(a) the compound of formula (I) or a pharmaceutical formulation according to (b), infra, for use in treatment or prophylaxis of pain, inflammation or pyresis in a mammal, including man;

(b) a pharmaceutical formulation comprising the compound of formula (I) in association with a pharmaceutically acceptable carrier therefor;

(c) a method for the preparation of a pharmaceutical formulation according to (b), supra, comprising bringing the compound of formula (I) into association with the pharmaceutically acceptable carrier; and (d) a method for the treatment or prophylaxis of pain, inflammation or pyresis in a mammal, including man, comprising the administration to said mammal of a non-toxic, effective analgesic, anti-inflammatory or antipyretic amount of the compound of formula (I) or of a pharmaceutical formulation according to (b), supra.

The following examples illustrate the invention but should not be taken to constitute a limitation thereof.

REFERENCE EXAMPLE A

Preparation of 3,4-Methylenedioxy acetanilide 3,4-Methylenedioxy aniline (27.4 g, 0.2 mole, obtained from Aldrich Chemical Co. No. 16, 149-7, m.p. 39°-41° C.), water (300 ml) and acetic anhydride (25-27 g) were stirred together at room temperature for from 1 to 2 hours. The product was suction-filtered, washed with cold water and recrystallised twice from ethyl acetate to afford 3,4-methylenedioxy acetanilide (23 g, 64%) m.p. 135°-137° C.

Analysis: Calculated for $C_9H_9NO_3$ (179.177 g): C, 60.33; H, 5.06; N, 7.82%. Found: C, 60.31; H, 5.03; N, 7.90%.

EXAMPLE I

Mild Analgesic Activity

A. Acetic Acid Writhing Test (AAWT)

Using the procedure described by Koster et al. in *Fed. Proc.* 18, 412 (1959) and Vinegar et al. in *Handbook of Experimental Pharmacology*, 50-2, ch. 26, *Anti-inflammatory Drugs*, Ed J. R. Vane and S. H. Ferreria (1978), the acetic acid writhing test was performed, using both the mouse and the rat, to demonstrate the mild analgesic activity of the compound of formula (I). Comparative results are given in Table I.

B. Trypsin Hyperalgesic Assay (THA)

This assay quantitatively measures analgesia and is designed to be unaffected by compounds possessing anti-inflammatory activity. A modification of the procedure described by Vinegar et al. in *Eur. J. Pharmacol.* 37, 23, (1976) was used to demonstrate the analgesic activity of the compound of formula (I) and certain known analgesics. The comparative results are given in Table I.

TABLE I

Analgesic Activity
All results are $ED_{50}$ mg/kg (p.o.)

| Assay | Aspirin | Acetaminophen | Compound of formula (I) | Phenacetin |
|---|---|---|---|---|
| (THA) Rat Hindlimb | Inactive at 360 | 95 ± 17.2 | 20 ± 5.1 | 69 ± 11.6 |
| Duration of Analgesia Time in hours to reduce 1.5 × THA $ED_{50}$ to 40% inhibition | — | — | 8.0 | 5.7 |
| AAWT Rat | 21 ± 3.4 | 127 ± 16.4 | 50 ± 0.6 | 46 ± 10.1 |
| Mouse | 301 ± 21.1 | 301 ± 11.5 | — | 116 ± 14.5 |

EXAMPLE II

Acute Anti-Inflammatory Activity

A. Carrageenin Pleurisy Assay (CPA)

Following the procedure described by Vinegar et al. in *European J. Rheumatology and Inflammation*, 1, 204, (1978) the acute anti-inflammatory activity of the compound of formula (I) was compared with that of known anti-inflammatory drugs. Two assays were performed: in the first, the average 3 hr exudate volume for each drug-treated group was determined and the % inhibition relative to solvent-fed control animals calculated, the $ED_{50}$ being the dose required to reduce the 3 hr exudate volume by 50%; in the second, the number of mobilized neutrophils was quantified and the % inhibition relative to solvent-fed control animals calculated, the $ED_{50}$ being the dose required to reduce the number of neutrophils mobilized at 3 hrs by 50%. The results are shown in Table II.

TABLE II

| Assay | Aspirin | Acetaminophen | Compound of formula (I) | Phenacetin |
|---|---|---|---|---|
| (CPA) $ED_{50}$ - mg/kg p.o. | | | | |
| Vol. | 28 ± 3.2 | 172 ± 22.4 | 34 ± 2.2 | 102 ± 14.6 |
| Cells | 75 ± 7.5 | 189 ± 48.6 | 49 ± 6.8 | 110 ± 15.5 |
| Local - mg/rat | 0.04 | Inactive at 1.0 | Inactive at 1.0 | Inactive at 1.0 |
| Duration of AI Activity Time in hrs to reduce 2 × CP cell $ED_{50}$ to 40% inhibition of Vol. | | | | |
| Vol. | 35.0 | 2.2 | (6) | 10.5 |
| Cells | 3.0 | 3.8 | 6 | 7.0 |
| AI Activity in Adrex CP p.o. | | | | |
| Vol. | Active | Active | Active | Weakly Active |
| Cells | Inactive | Weakly Active | Active | Inactive |

EXAMPLE III

Antipyretic Activity

The Yeast-Induced Hyperthermia Assay was used according to the procedure described by Khalili-Varasteh et al. in *Arch. Int. Pharmacodyn.* 219, 149-159, (1976) to demonstrate the antipyretic activity of the compound of formula (I) and certain known antipyretics in the rat. The results are shown in Table III.

TABLE III

| Assay | Aspirin | Acetaminophen | Compound of formula (I) | Phenacetin |
|---|---|---|---|---|
| Rat Yeast Hyperthermia p.o. $ED_{50}$ mg/kg | 50 ± 8.1 | 72 ± 8.6 | 57 | 55 ± 28.6 |

EXAMPLE IV

Acute Toxicity Assay

Four non-fasted male rats of 160-250 gram body weight were used for each dose level. The compound was injected by the indicated route and the symptom onset time, the intensity of the effect and the duration during a 4 hour observation period are recorded. The $LD_{50}$ estimated is based on a 7 day observation and is determined by the method of Miller and Tainter (Proc. Soc. Exp. Biol. Med. 57:261, 1944).

In addition to the data shown in Table (IV) it was found that the compound of formula (I) does not produce gastric damage in the rat after 80 mg/kg whereas a single oral dose of 30 mg/kg aspirin produces ulcers and haemorrhages.

TABLE IV A

ACUTE TOXICITY

| Assay $LD_{50}$ - mg/kg | Aspirin | Acetaminophen | Compound of formula (I) | Phenacetin |
|---|---|---|---|---|
| Mouse, i.p. | 220 | 880 | 250 | 620 |
| Mouse, p.o. | 1100 | 1640 | 660 | 2500 |
| Rat, i.p. | 500 | 1640 | 410 | 900 |
| Rat, p.o. | 1610 | 2000 | 1000 | 2900 |

TABLE IV B

ACUTE TOXICITY

| Assay | Acetaminophen | Compound of formula (I) | Phenacetin |
|---|---|---|---|
| Hepatic Gluathione Depletion | + | | + |
| @ 40% of LD$_{50}$, i.p. in mouse | | | |
| 90% depletion over a 5 hr period - | | | |
| 40% depletion or less over a 5 hr period | | | |
| Histopathology | | | |
| Mouse Liver | + | — | — |
| Mouse Kidney | + | — | — |
| Rat Liver | + | — | — |
| Rat Kidney | + | — | — |
| @ 40% LD$_{50}$, i.p. | | | |
| Methemoglobinemia-(Cyanosis) mg/kg p.o. | Rat No @ 500 | No @ 500 | Yes @ 500 |
| | Dog No @ 100 | Slight @ 200 | Yes @ 100 |

+ Damage observed
− No damage observed

EXAMPLE A

Suppository

| Ingredient | Amount per suppository |
|---|---|
| Active compound | 325.0 mg |
| Witepsol H 25, q.s. or Wecobee Base | 2.0 g |

Wecobee is the trade name of a hydrogenated carboxylic acid.

The finely-ground active compound was mixed with the melted suppository base (either Witepsol H25 or Wecobee base), poured into moulds and allowed to cool to afford the desired suppositories.

EXAMPLE B

Syrup

| Ingredient | Amount per 5 ml |
|---|---|
| Active Compound | 325.0 mg |
| Glycerin | 500.0 mg |
| Sucrose | 3500.0 mg |
| Methylparabens | 5.0 mg |
| Sodium Benzoate | 5.0 mg |
| Cherry Flavour | 0.005 ml |
| Colouring | q.s. |
| Ethanol | 3.0 ml |
| Water, q.s. | 5.0 ml |

Glycerol, sucrose, methylparabens, and flavouring were combined in 80% of the total batch quantity of water. Sodium benzoate, colouring and the active compound were dissolved in ethanol, then the two solutions were mixed and clarified by filtration.

EXAMPLE C

Tablet

| Ingredient | Amount per tablet (mg) |
|---|---|
| Active Compound | 325.0 |
| Lactose | 125.0 |
| Corn Starch | 50.0 |
| Polyvinylpyrrolidone | 3.0 |
| Stearic acid | 1.0 |
| Magnesium stearate | 1.0 |

The active compound was finely ground and intimately mixed with the powdered carriers lactose, corn starch, polyvinylpyrrolidone, magnesium stearate and stearic acid. The formulation was then compressed to afford one tablet weighing 505 mg.

EXAMPLE C

Hard Gelatin Capsule

| | Amount per capsule (mg) |
|---|---|
| Active Compound | 325.0 |
| Lactose | 174.0 |
| Corn Starch | 174.0 |
| Stearic Acid | 2.0 |

The finely ground active compound was mixed with the powdered carriers lactose, corn starch and stearic acid, and packed into gelatin capsules.

EXAMPLE E

Lozenges

| | Amount per tablet (mg) |
|---|---|
| Active Compound | 325.0 |
| Sucrose | 125.0 |
| Mannitol | 125.0 |
| Polyvinylpyrrolidone | 5.0 |
| Stearic Acid | 1.0 |
| Magnesium Stearate | 1.0 |

The sucrose and mannitol are wet granulated with a solution the polyvinyl pyrrolidone in ethanol/water (1:1). The resultant granules are sieved, dried, mixed with the stearic acid and magnesium stearate and compressed to provide lozenges.

EXAMPLE F

Soft Gelatin capsule

| Ingredient | Amount per capsule (mg) |
|---|---|
| Active Compound | 325.0 |
| Polyoxyethylene sorbitol mono-oleate | 40.0 |
| Maize oil | 535.0 |

The active compound was dispersed in a mixture of the Polyoxyethylene sorbitol mono-oleate and maize oil. The resultant mixture was encapsulated in soft gelatin at a unit dose of 900 mg.

EXAMPLE G

Sustained release tablet

| | Amount per tablet (mg) |
|---|---|
| Active Compound | 325.0 |
| Microcrystalline cellulose | 100.0 |
| Corn Starch | 50.0 |
| Polyvinylpyrrolidone | 3.0 |
| Sodium starch glycollate | 10.0 |
| Magnesium stearate | 1.0 |
| Polymethylmethacrylate | 5.0 |
| Carnauba Wax | 0.5 |

| | Amount per tablet (mg) |
|---|---|
| Titanium dioxide | 1.0 |

The active compound was mixed with the starch and microcrystalline cellulose. This mixture was granulated with a solution of polyvinylpyrrolidone in ethanol/water solution. The mixture was dried. Sodium starch glycollate and magnesium stearate were added and the whole compressed to afford a tablet weighing 489 mg. The tablet was coated using a solution of polymethylmethacrylate in methylene chloride containing titanium dioxide in dispersion and polished with carnauba wax.

What we claim is:

1. A method for the treatment or prophylaxis of a condition selected from pain, inflammation and pyresis in a mammal comprising the administration to said mammal of a non-toxic, effective analgesic, anti-inflammatory or antipyretic amount of a compound of N-(1,3-benzodioxol-5-yl) acetamide.

2. A method for the treatment or prophylaxis of a condition selected from pain, inflammation and pyresis in a mammal comprising the administration to said mammal of a non-toxic, effective analgesic, anti-inflammatory or anti-pyretic amount of a pharmaceutical formulation containing the compound N-(1,3-benzodioxol-5-yl) acetamide and a pharmaceutically acceptable carrier therefor.

3. A method according to claim 1 or 2 wherein the compound is administered in the range of from 1 to 100 mg/kg mammal bodyweight per day.

4. A method according to claim 1 or 2 wherein the compound of formula (I), as defined in claim 1, is administered in the range of from 0.5 to 30 mg/kg mammal bodyweight per dose.

5. A method according to claim 1 or 2 for the treatment or prophylaxis of a condition selected from headache, toothache, rheumatoid arthritis, osteoarthritis and pyresis associated with pain and inflammation.

6. The method of claim 1 or 2 in which the mammal is a human.

7. A pharmaceutical formulation for treatment or prophylaxis of a condition selected from pain, inflammation and pyresis comprising an effective amount of the compound N-(1,3-benzodioxol-5-yl) acetamide in association with a pharmaceutically acceptable carrier, said formulation in the form of a tablet, capsule, syrup, lozenge or suppository.

8. A pharmaceutical formulation for treatment or prophylaxis of a condition selected from pain, inflammation and pyresis comprising an effective amount of the compound N-(1,3-benzodioxol-5-yl) acetamide in association with a pharmaceutically acceptable sterile carrier, said formulation in a form for parenteral administration.

* * * * *